United States Patent
Petersen (10) Patent No.: US 11,806,517 B2
(45) Date of Patent: Nov. 7, 2023

(54) IMPELLER DISPLACEMENT BASED FLOW ESTIMATION

(71) Applicant: TC1 LLC, St. Paul, MN (US)

(72) Inventor: Ethan Falk Petersen, Oakland, CA (US)

(73) Assignee: TC1 LLC, St. Paul, MN (US)

(*) Notice: Subject to any disclaimer, the term of this patent is extended or adjusted under 35 U.S.C. 154(b) by 370 days.

(21) Appl. No.: 16/884,956

(22) Filed: May 27, 2020

(65) Prior Publication Data

US 2020/0282121 A1 Sep. 10, 2020

Related U.S. Application Data

(62) Division of application No. 15/212,721, filed on Jul. 18, 2016, now Pat. No. 10,722,630.

(Continued)

(51) Int. Cl.
*A61M 60/419* (2021.01)
*A61M 60/422* (2021.01)
(Continued)

(52) U.S. Cl.
CPC ........ *A61M 60/419* (2021.01); *A61M 60/178* (2021.01); *A61M 60/232* (2021.01); *A61M 60/237* (2021.01); *A61M 60/422* (2021.01); *A61M 60/538* (2021.01); *A61M 60/148* (2021.01); *A61M 60/818* (2021.01); *A61M 60/824* (2021.01); *A61M 2205/332* (2013.01);
(Continued)

(58) Field of Classification Search
CPC .......................... A61M 60/50; A61M 60/419
See application file for complete search history.

(56) References Cited

U.S. PATENT DOCUMENTS 5,695,471 A 12/1997 Wampler
5,708,346 A 1/1998 Schob
(Continued)

FOREIGN PATENT DOCUMENTS

EP 1812094 8/2007
EP 3164168 5/2017
(Continued)

*Primary Examiner* — Jennifer Pitrak McDonald
*Assistant Examiner* — Jennifer L Ghand
(74) *Attorney, Agent, or Firm* — Kilpatrick Townsend & Stockton LLP (57) ABSTRACT

A circulation assist system measures impeller displacement for use in estimating a blood flow rate related parameter. A circulation assist system includes a blood pump and a controller. The blood pump includes an impeller magnetically supported within a blood flow channel. The blood pump includes one or more sensors configured to generate output indicative of displacement of the impeller along the blood flow channel induced by a blood-flow induced thrust load applied to the impeller. The controller is configured to process the output generated by the one or more sensors to determine the displacement of the impeller along the blood flow channel. The controller is configured to process the determined displacement of the impeller to estimate at least one of the thrust load applied to the impeller, a pressure differential of the blood impelled through the blood flow channel, and a flow rate of blood pumped by the blood pump.

19 Claims, 8 Drawing Sheets

Related U.S. Application Data (60) Provisional application No. 62/194,700, filed on Jul. 20, 2015.

(51) Int. Cl.
   *A61M 60/237* (2021.01)
   *A61M 60/232* (2021.01)
   *A61M 60/538* (2021.01)
   *A61M 60/178* (2021.01)
   *A61M 60/148* (2021.01)
   *A61M 60/818* (2021.01)
   *A61M 60/824* (2021.01)

(52) U.S. Cl.
   CPC .............. *A61M 2205/3334* (2013.01); *A61M 2205/3344* (2013.01); *A61M 2210/125* (2013.01); *A61M 2210/127* (2013.01); *A61M 2230/04* (2013.01)

(56) References Cited

U.S. PATENT DOCUMENTS

| | | |
|---|---|---|
| 5,725,357 A | 3/1998 | Nakazeki et al. |
| 5,888,242 A | 3/1999 | Antaki et al. |
| 5,947,703 A | 9/1999 | Nojiri et al. |
| 5,951,263 A | 9/1999 | Taylor et al. |
| 6,053,705 A | 4/2000 | Schob et al. |
| 6,071,093 A | 6/2000 | Hart |
| 6,100,618 A | 8/2000 | Schoeb et al. |
| 6,116,862 A | 9/2000 | Rau et al. |
| 6,135,943 A | 10/2000 | Yu et al. |
| 6,176,822 B1 | 1/2001 | Nix et al. |
| 6,186,665 B1 | 2/2001 | Maher et al. |
| 6,201,329 B1 | 3/2001 | Chen |
| 6,222,290 B1 | 4/2001 | Schoeb et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schob |
| 6,351,048 B1 | 2/2002 | Schob et al. |
| 6,355,998 B1 | 3/2002 | Schoeb et al. |
| 6,468,041 B2 | 10/2002 | Ozaki |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,626,644 B2 | 9/2003 | Ozaki |
| 6,634,224 B1 | 10/2003 | Schob et al. |
| 6,688,861 B2 | 2/2004 | Wampler |
| 6,707,200 B2 | 3/2004 | Carroll et al. |
| 6,817,836 B2 | 11/2004 | Nose et al. |
| 6,879,074 B2 | 4/2005 | Amrhein et al. |
| 6,949,066 B2 | 9/2005 | Bearnson et al. |
| 6,991,595 B2 | 1/2006 | Burke et al. |
| 7,112,903 B1 | 9/2006 | Schob |
| 7,138,776 B1 | 11/2006 | Gauthier et al. |
| 7,150,711 B2 | 12/2006 | Nusser et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,591,777 B2 | 9/2009 | LaRose |
| 7,645,225 B2 | 1/2010 | Medvedev et al. |
| 7,699,586 B2 | 4/2010 | LaRose et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | LaRose et al. |
| 7,951,062 B2 | 5/2011 | Morello |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,157,720 B2 | 4/2012 | Marseille et al. |
| 8,303,482 B2 | 11/2012 | Schima et al. |
| 8,323,174 B2 | 12/2012 | Jeevanandam et al. |
| 8,382,830 B2 | 2/2013 | Maher et al. |
| 8,449,444 B2 | 5/2013 | Poirier |
| 8,506,470 B2 | 8/2013 | LaRose et al. |
| 8,506,471 B2 | 8/2013 | Bourque |
| 8,517,699 B2 | 8/2013 | Horvath |
| 8,556,795 B2 | 10/2013 | Bolyard et al. |
| 8,562,508 B2 | 10/2013 | Dague et al. |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,764,621 B2 | 7/2014 | Badstibner et al. |
| 8,870,739 B2 | 10/2014 | LaRose et al. |
| 8,882,477 B2 | 11/2014 | Fritz, IV et al. |
| 8,897,873 B2 | 11/2014 | Schima et al. |
| 8,956,275 B2 | 2/2015 | Bolyard et al. |
| 9,265,870 B2 | 2/2016 | Reichenbach et al. |
| 9,511,179 B2 | 12/2016 | Casas et al. |
| 9,901,666 B2 | 2/2018 | Cotter |
| 2001/0031210 A1 | 10/2001 | Antaki et al. |
| 2003/0163019 A1 | 8/2003 | Goldowsky |
| 2003/0193252 A1 | 10/2003 | Locke |
| 2003/0223879 A1 | 12/2003 | Yanai et al. |
| 2004/0228724 A1 | 11/2004 | Capone et al. |
| 2004/0241019 A1 | 12/2004 | Goldowsky |
| 2005/0071001 A1 | 3/2005 | Jarvik |
| 2006/0024182 A1* | 2/2006 | Akdis .................. A61M 60/82 417/357 |
| 2007/0078293 A1 | 4/2007 | Shambaugh, Jr. et al. |
| 2007/0119246 A1 | 5/2007 | Miyakoshi et al. |
| 2008/0021394 A1 | 1/2008 | LaRose et al. |
| 2009/0203957 A1 | 8/2009 | LaRose et al. |
| 2010/0130809 A1 | 5/2010 | Morello |
| 2010/0241223 A1 | 9/2010 | Lee et al. |
| 2010/0327687 A1 | 12/2010 | Iannello et al. |
| 2011/0071337 A1 | 3/2011 | Thompson et al. |
| 2011/0237863 A1 | 9/2011 | Ricci et al. |
| 2011/0243759 A1 | 10/2011 | Ozaki et al. |
| 2011/0313237 A1 | 12/2011 | Miyakoshi et al. |
| 2012/0046514 A1 | 2/2012 | Bourque |
| 2012/0095281 A1 | 4/2012 | Reichenbach et al. |
| 2012/0226097 A1 | 9/2012 | Smith et al. |
| 2012/0245681 A1 | 9/2012 | Casas et al. |
| 2013/0030240 A1 | 1/2013 | Schima et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2013/0331934 A1 | 12/2013 | Kabir et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |
| 2015/0367048 A1 | 12/2015 | Brown et al. |
| 2016/0144092 A1 | 5/2016 | Casas et al. |
| 2016/0235898 A1 | 8/2016 | Yanai et al. |
| 2016/0375187 A1* | 12/2016 | Lee .................... A61M 60/205 600/16 |
| 2017/0021070 A1 | 1/2017 | Petersen |
| 2017/0021071 A1* | 1/2017 | Cotter ................. A61M 60/232 |
| 2020/0282121 A1* | 9/2020 | Petersen ............. A61M 60/419 |

FOREIGN PATENT DOCUMENTS

| | | |
|---|---|---|
| WO | 2004017818 | 3/2004 |
| WO | 2014197558 | 12/2014 |

\* cited by examiner

IMPELLER DISPLACEMENT BASED FLOW ESTIMATION

CROSS-REFERENCES TO RELATED APPLICATIONS

The present application is a Divisional of U.S. patent application Ser. No. 15/212,721 filed Jul. 18, 2016 (now U.S. Pat. No. 10,722,630); which claims the benefit of U.S. Provisional Appln No. 62/194,700 filed Jul. 20, 2015, the disclosures of which are incorporated herein by reference in their entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

The flow rate of blood pumped by a VAD is an important parameter for both control of the blood pump and for informing a health care professional regarding the level of circulatory support provided to the patient by the VAD. Direct measurement of blood flow rate has several drawbacks with existing technology. For example, the addition of components (e.g., a flow sensor) may increase complexity and reduce reliability. It is also generally undesirable to place structures in the flowpath because they can lead to thrombosis. Moreover, existing flow sensors suffer from drift and other factors which contribute to imprecise measurements over time.

Accordingly, existing VADs generally rely on an estimation of flow rate through the pump by indirect measurements. For example, the blood flow rate in a VAD can be estimated based on the amount of electrical power consumed by the VAD.

There is a need for improved devices and methods for measuring or estimating flow rate in a pump.

Additionally, there is the need for devices and methods for measuring clinical and/or pump parameters.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Improved blood circulation assist systems and related methods measure thrust load applied to a rotating impeller and estimate a flow rate of blood pumped by the blood pump based on impeller rotational speed and the thrust load. The thrust load can be measured via a sensor generating output indicative of a reaction force generated by the thrust load. The thrust load can also be measured via measurement of a displacement of the impeller induced by the thrust load. In at least some operational regimes, flow rate estimation based on the thrust load and impeller rotational speed is more accurate than flow rate estimation based on power consumption and impeller rotational speed.

Thus, in one aspect, a blood pump for a circulation assist system estimates a flow rate of blood pumped by the blood pump based on impeller rotational speed and thrust load applied to the impeller by blood impelled by the impeller. The blood pump includes a housing, an impeller, a motor stator, a support member, a sensor, and a controller. The housing forms a blood flow channel. The impeller is disposed within the blood flow channel. The motor stator is mounted to the housing and operable to magnetically rotate the impeller. The support member is coupled to the housing. The support member reacts a thrust load applied to the impeller by blood impelled through the blood flow channel by the impeller. The sensor generates a sensor output indicative of a magnitude of the thrust load reacted by the support member. The controller is operatively coupled with the motor stator and the sensor. The controller is configured to determine an impeller rotational speed for the impeller and estimate a flow rate of blood pumped by the blood pump based on the impeller rotational speed and the sensor output.

In many embodiments, the impeller is supported by the support member. For example, the impeller can be supported via a support bearing supported by the support member and the thrust load reacted by the support member is applied to the support member via the support bearing. An inlet stator can include the support member and be used to support the support bearing and/or the impeller.

In many embodiments, the sensor output is indicative of deformation of the support member induced by the thrust load reacted by the support member. For example, the sensor can include a strain gauge coupled to the support member and the sensor output can be indicative of strain in the support member induced by the thrust load reacted by the support member.

In many embodiments, the sensor output is indicative of a deflection of the support member induced by the thrust load reacted by the support member. For example, the sensor can include a deflection measuring sensor coupled to the support member and configured to measure a deflection of the support member induced by the thrust load reacted by the support member.

The systems and methods described herein allow for estimation of a pressure drop across the pump. In turn, the pressure estimate can be used clinically or to optimize operation of the pump. For example, an LVAD is typically connected to pull blood from the left ventricle and pump it to the aorta. The pressure drop across the pump is thus indicative of the difference between the left ventricular pressure and the aortic pressure. In other words, the pressure across the pump is representative of the pressure across the aortic valve. Knowing the pressure across the aortic valve has clinical value in its own right, and is useful in helping the clinician understand the functioning of the patient's heart. Accordingly, in many embodiments, the controller is configured to estimate a differential pressure across the pump based on the sensor output and output the pressure differential to an output device for output to a person. For example, the controller can determine the magnitude of the thrust load reacted by the support member and determine the differential pressure across the pump corresponding to the magnitude of the thrust load. The controller can then output the estimated pressure differential for display on a display device. In many embodiments, the blood pump is configured to pump blood from the patient's left ventricle to the patient's aorta. In such embodiments, the pressure differential corresponds to the pressure difference between the patient's left ventricle and the patient's aorta.

In many embodiments, the motor stator is coupled to the housing via the support member and transfers the thrust load applied to the impeller to the support member. For example, in many embodiments, the thrust load applied to the impeller is reacted via passive magnetic attraction between the impeller and the motor stator and the motor stator is coupled to the housing via the support member so as to react at least a portion of the thrust load reacted by the motor stator.

In another aspect, a method is provided for estimating blood flow rate in a blood circulation assist system. The method includes controlling a motor stator to magnetically rotate an impeller within a blood flow channel of a blood pump. A thrust load applied to the impeller by blood impelled through the blood flow channel by the impeller is reacted by a support member coupled to a housing of the blood pump. A sensor output indicative of a magnitude of the thrust load reacted by the support member is generated. An impeller rotational speed for the impeller is determined by a controller. A flow rate of blood impelled by the impeller is estimated by the controller based on the rotational speed and the sensor output.

In many embodiments, the method includes supporting the impeller via the support member. For example, the method can include supporting the impeller via a support bearing supported by the support member. The thrust load can be applied to the support member via the support bearing.

Any suitable sensor can be used in the method to generate the sensor output indicative of a magnitude of the thrust load reacted by the support member. For example, the sensor output can be indicative of strain in the support member induced by the thrust load reacted by the support member. The sensor output can be indicative of a deflection of the support member induced by the thrust load reacted by the support member.

The sensor output can be used to estimate other pump related parameters. For example, the method can include estimating, by the controller, a pressure differential across the blood pump based on the sensor output. The method can include outputting the pressure differential, by the controller, to an output device for output to a person.

In many embodiments of the method, the motor stator is coupled to the housing via the support member. In such embodiments, the method can further include reacting the thrust load applied to the impeller by the motor stator via passive magnetic attraction between the impeller and the motor stator and reacting the thrust load reacted by the motor stator by the support member.

In another aspect, a blood pump for a circulation assist system includes a housing, an impeller, a motor stator, at least one Hall-Effect sensor, and a controller. The housing forms a blood flow channel. The impeller is disposed within the blood flow channel. The motor stator is mounted to the housing and operable to magnetically rotate the impeller. A thrust load applied to the impeller by blood impelled through the blood flow channel by the impeller is reacted by the motor stator via passive magnetic attraction between the impeller and the motor stator. The at least one Hall-Effect sensor is configured to generate output indicative of a displacement of the impeller along the blood flow channel induced by the thrust load applied to the impeller. The controller is operatively coupled with the motor stator and the at least one Hall-Effect sensor. The controller is configured to determine an impeller rotational speed for the impeller, process the output generated by the at least one Hall-Effect sensor to determine the displacement of the impeller along the blood flow channel, and estimate a flow rate of blood pumped by the blood pump based on the impeller rotational speed and the displacement of the impeller. In many embodiments, the controller is further configured to estimate a differential pressure across the blood pump based on the displacement of the impeller.

In another aspect, a method is provided for estimating blood flow rate in a blood circulation assist system. The method includes controlling a motor stator to magnetically rotate an impeller within a blood flow channel of a blood pump. A thrust load applied to the impeller by blood impelled through the blood flow channel by the impeller is reacted via passive magnetic attraction between the impeller and the motor stator. Output generated by at least one Hall-Effect sensor is processed by a controller to determine a displacement of the impeller along the blood flow channel induced by the thrust load applied to the impeller. An impeller rotational speed for the impeller is determined by the controller. A flow rate of blood impelled by the impeller is estimated by the controller based on the impeller rotational speed and the displacement of the impeller. Many embodiments of the method further include estimating, by the controller, a pressure differential across the blood pump based on the displacement of the impeller.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
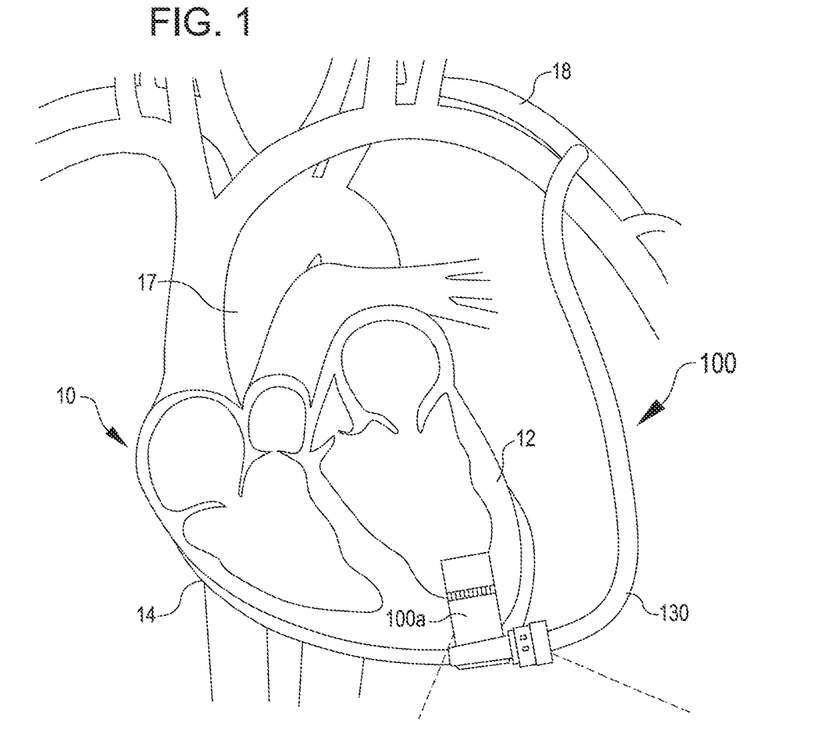
FIG. 1 illustrates a blood pump of a circulation assist system implanted within a patient, in accordance with many embodiments.

Referring now to the drawings, in which like reference numerals represent like parts throughout the several views, FIG. 1 shows a blood pump assembly 100 implanted in a patient's body to supplement, or in some cases replace, the natural pumping function of a heart 10. Aspects of the pump assembly 100 are similar to those disclosed in U.S. Pat. Nos. 5,951,263; 6,186,665; U.S. application Ser. No. 13/273,185 filed Oct. 13, 2011 and entitled PUMPING BLOOD; and U.S. application Ser. No. 12/394,244 filed Feb. 27, 2009 and entitled BLOOD FLOW METER, the entire contents of which patents and applications are incorporated herein by reference for all purposes. The blood pump assembly 100 includes a blood pump 100a, which can be implanted to receive blood from the heart 10, for example, from a left ventricle 12 of the heart 10. As shown, the blood pump 100a pumps blood through an outflow conduit 130 to the patient's circulatory system, for example, to an aorta 17 or a peripheral artery 18. The outflow conduit 130 for the blood pump 100a in FIG. 1 is connected to the peripheral artery 18 thereby assisting the patient's circulation in a manner that might be used for a partial support patient. For a full support patient the outflow conduit 130 is connected to the aorta 17. The blood pump assembly 100 can also be implanted such that the blood pump 100a receives blood from a right ventricle 14 of the heart 10 and supplies blood to, for example, a pulmonary artery.

Figure 2:
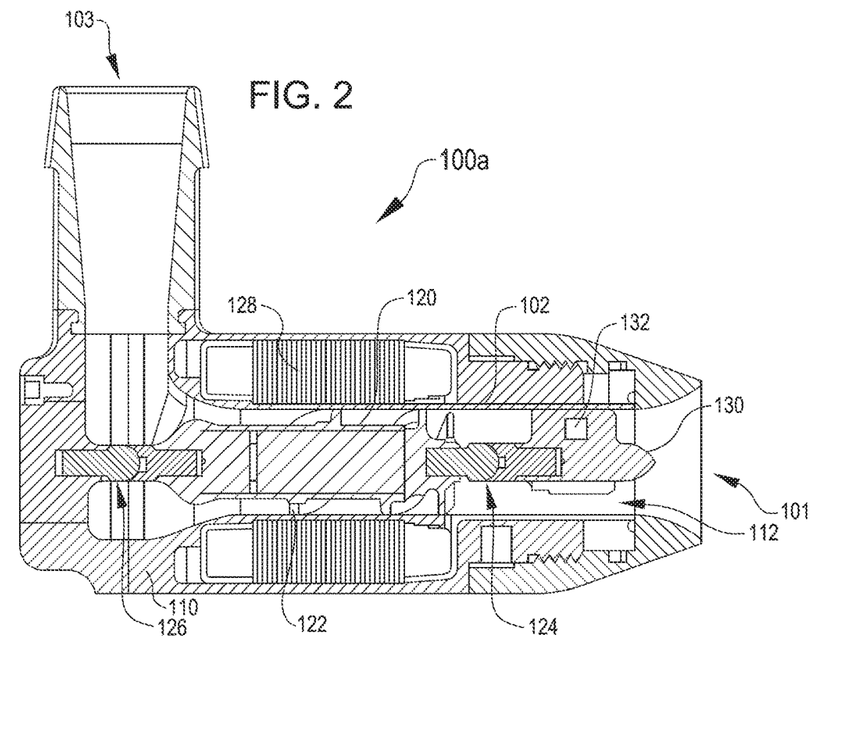
FIG. 2 is a cross-sectional view of a blood pump in which an impeller is supported via end bearings and a thrust load applied to the impeller is reacted into an inlet stator via one of the end bearings, in accordance with many embodiments.

Referring to FIG. 2, the blood pump 100a includes a housing 110 that defines a blood flow channel 112. Blood enters the blood flow channel 112 through an inlet 101, passes through a central tubular region 102 of the housing 110, and exits through an outlet 103. The housing 110 contains a motor stator 128, which drives rotation of an impeller 120 located in the blood flow channel 112. As the impeller 120 rotates, blades 122 on the impeller 120 impart energy to the blood flow, resulting in pressure and blood flow at the outlet 103. The impeller 120 is suspended in the blood flow channel 112 by fore and aft mechanical, blood-immersed bearings 124, 126 that limit axial translation of the impeller 120. The bearings 124, 126 also limit the impeller from shifting off its axis of rotation.

The blood pump 100a includes an inlet stator 130, which is connected to the housing 110 and supports the inlet side bearing 124. A strain gauge 132 is mounted to the inlet stator 130 and generates output indicative of strain in the inlet stator 130 induced by reacting the thrust load applied to the inlet side bearing 124 by the impeller 120. The output from the strain gauge 132 is processed to determine the magnitude of the thrust load, which is then used in combination with the rotational rate of the impeller 120 to estimate flow rate of the blood pumped by the blood pump 100a.

Figure 3:
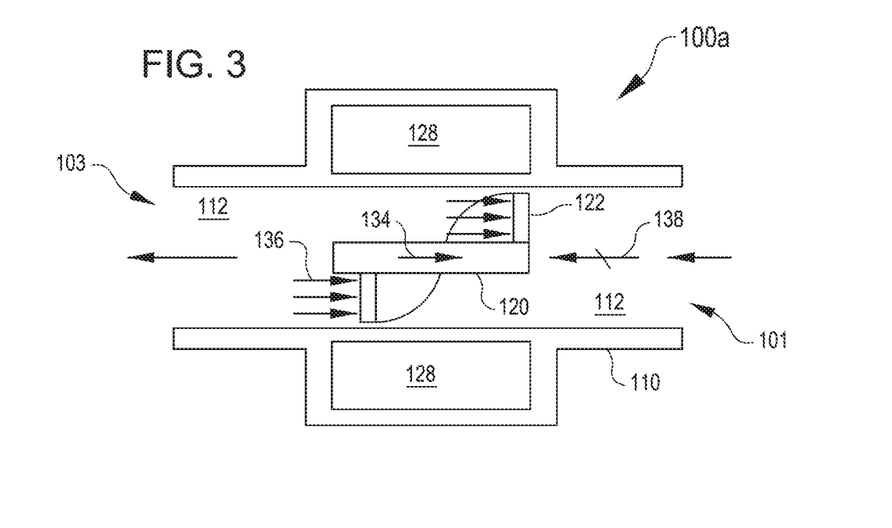
FIG. 3 is a simplified schematic diagram illustrating the generation of the thrust load on the impeller of the blood pump of FIG. 2.

FIG. 3 is a simplified schematic diagram illustrating the generation of a thrust load 134 on the impeller 120 of the blood pump 100a. Rotation of the impeller 120 impels the blood flow along the blood flow channel 112 and out of the outlet 103. The rotating impeller 120 applies a net force to the blood, which in response exerts the thrust load 134 on the impeller 120. The pressure applied on the impeller 120 by the blood (e.g., net pressure forces 136 applied to the blades 122) generates the thrust load 134. The impeller 120 transfers the thrust load 134 to the inlet side bearing 124. As seen from the perspective of the impeller 120, the inlet side bearing 124 applies a reaction force 138 to the impeller 120. As would be understood by one of skill, for every force there is an equal and opposite force, accordingly, the reaction force 138 is generally equal in magnitude and opposite in direction to the thrust load 134 applied to the impeller 120 by the blood impelled along the blood flow channel 112 by the impeller 120. The thrust load 134 applied to the inlet side bearing 124 is reacted into the housing 110 via the inlet stator 130, thereby inducing strain in the inlet stator 130. The strain gauge 132 is attached to the inlet stator 130 so that the strain induced in the inlet stator 130 by the thrust load 134 induces a corresponding strain in the strain gauge 132. The strain in the strain gauge 132 induces a change in the resistance of the strain gauge 132, which is measured using known techniques. The change in the resistance of the strain gauge 132 is used to determine the corresponding thrust load 134 using any suitable known approach including calibration.

Figure 4:
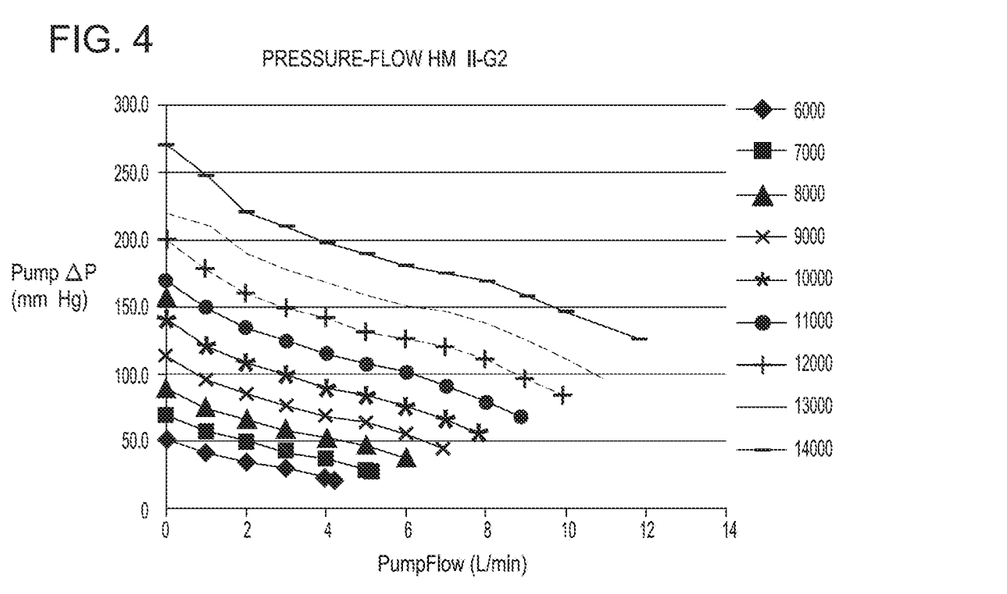
FIG. 4 is a plot of differential pressure across the blood pump of FIG. 2 as a function of flow rate and impeller rotation rate.

The instantaneous rate of flow of blood through the blood pump 100a can be estimated based on the determined thrust load 134 and the rotational rate of the impeller 120. For example, FIG. 4 is a plot of differential pressure across the blood pump 110a as a function of flow rate and impeller rotation rate. The differential pressure across the blood pump 110a can be calculated by dividing the determined thrust load 134 by a suitable cross-sectional reference area for the blood flow channel 112. The rotational rate of the impeller 120 can be determined using the approaches as described herein. The rotational rate of the impeller 120 and the differential pressure can be used to determine a flow rate of blood through the pump 120 using the data of FIG. 4. For example, for a determined thrust load 134 corresponding to a differential pressure of 150 mm Hg and an impeller rotational rate of 12,000 rpm, the corresponding flow rate of blood is about 3.0 L/min.

In many embodiments, a suitable electronic controller is operatively coupled with the motor stator 128 and the strain gauge 132. The controller can control the motor stator 128 via control of current applied to windings of the motor stator 128 so as to control rotation of the impeller 120. As described herein, the controller can monitor a rotational rate of the impeller 120 using any suitable known approach, such a via control of the motor stator 128 and/or via processing output from one or more Hall-Effect sensors to determine the rotational rate of the impeller 120. The controller can be operatively coupled with the strain gauge 132 so as to be able to measure changes in resistance of the strain gauge 132 and thereby determine a corresponding thrust load applied by the impeller 120 to the inlet stator 130 via the inlet side bearing 124. The controller can then process the thrust load (or a differential pressure calculated from the thrust load) and the impeller rotation rate to generate a corresponding flow rate of blood via data relating the thrust load (or corresponding differential pressure) and the rotation rate to flow rate.

Flow Estimation in Magnetically Levitated Impeller Pumps

Figure 5:
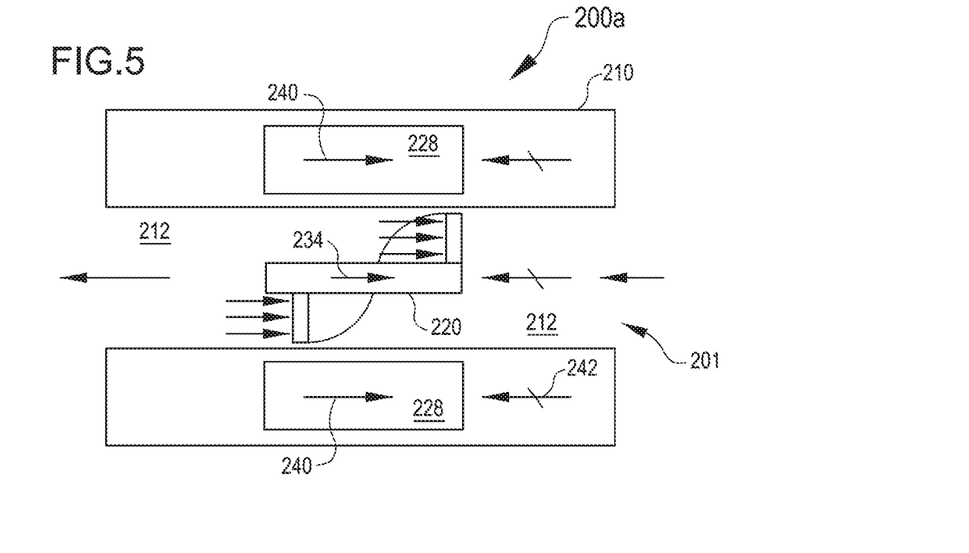
FIG. 5 is a simplified schematic diagram illustrating a blood pump in which a thrust load applied to an impeller is reacted by a support member supporting a motor stator used to rotate and magnetically position the impeller within a blood flow channel of the blood pump, in accordance with many embodiments.

FIG. 5 is a simplified schematic diagram illustrating alternative embodiments of a blood pump 200a in which a thrust load 234 applied to an impeller 220 is reacted by one or more support members supporting a motor stator 228 configured to rotate and magnetically position the impeller 220 within a blood flow channel 212 of the blood pump 220a. In accordance with embodiments described herein, the impeller 220 is magnetically levitated within the blood flow channel 212 via the motor stator 228. The radial position of the impeller 220 within the blood flow channel (perpendicular to the inflow direction) is controlled via active control of current applied to the levitation coils of the motor stator. The axial position of the impeller 220 (parallel to the blood flow direction) along the blood flow channel 212 is passively controlled via passive magnetic attraction between the impeller 220 and stator poles of the motor stator 228. The thrust load 234 applied to the impeller 220 positions the impeller 220 along the blood flow channel 212 to a position where the passive magnetic attraction between the impeller 220 and the motor stator 228 has an axial component (parallel to the blood flow direction) equal and opposite to the thrust load 234. The axial component of the passive magnetic attraction between the impeller 220 and the motor stator 228 thereby applies an axial thrust load 240 to the motor stator 228, thereby pushing the motor stator 228 in a direction parallel to the blood flow and towards the inlet 201. The motor stator 228 can be mounted to the housing via one or more support members such that the axial thrust load 240 is transferred to the housing 210 via the one or more support members. From the perspective of the motor stator 228, the one or more support members apply a reaction load 242 onto the motor stator 228, thereby balancing the axial thrust load 240 applied to the motor stator 228 via the passive magnetic attraction between the motor stator 228 and the impeller 220. One or more of the one or more supports can include a suitable number of strain gauges operatively coupled with a controller configured to monitor the strain gauges to determine the thrust load 240 applied to the motor stator 228 and thereby determine the corresponding thrust load 234 applied to the impeller 220. As described above, the thrust load 234 and the rotation rate of the impeller 220 can be used to estimate the flow rate of blood through the blood pump 200a.

Figure 6:
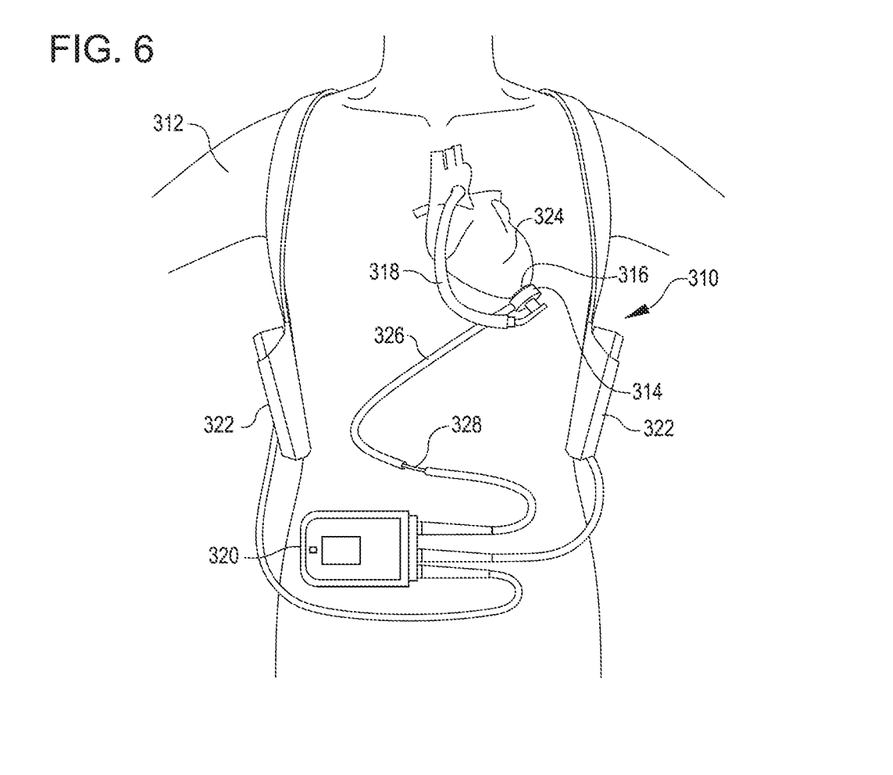
FIG. 6 is an illustration of a mechanical circulatory support system implanted in a patient's body, in accordance with many embodiments.
Figure 7:
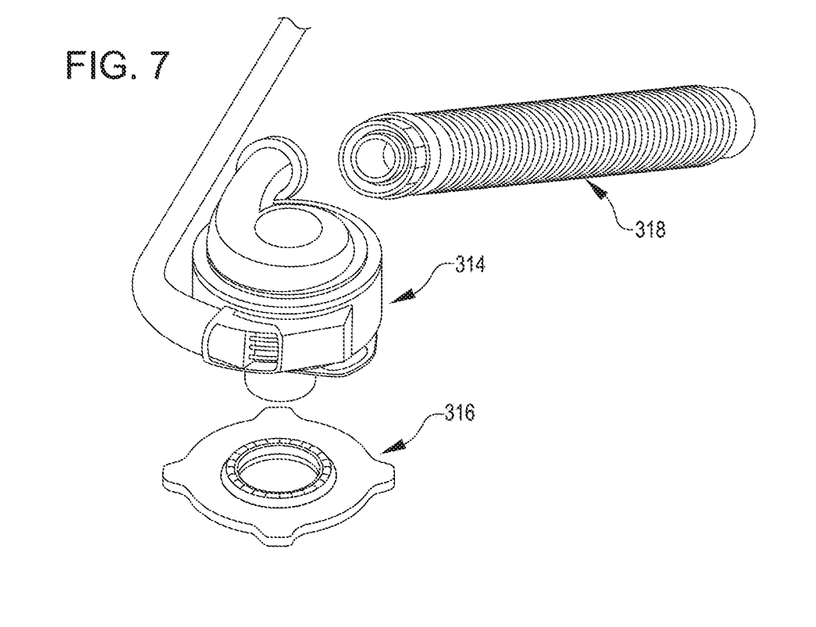
FIG. 7 is an exploded view of certain components of the circulatory support system of FIG. 6.

FIG. 6 is an illustration of a mechanical circulatory support system 310 implanted in a patient's body 312. The mechanical circulatory support system 310 includes an implantable blood pump assembly 314, a ventricular cuff 316, an outflow cannula 318, an external system controller 320, and power sources 322. The implantable blood pump assembly 314 can include a VAD that is attached to an apex of the left ventricle, as illustrated, or the right ventricle, or both ventricles of the heart 324. The VAD can include a centrifugal pump (as shown) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIG. 6 and FIG. 7, the blood pump assembly 314 can be attached to the heart 324 via the ventricular cuff 316, which can be sewn to the heart 324 and coupled to the blood pump 314. The other end of the blood pump 314 connects to the ascending aorta via the outflow cannula 318 so that the VAD effectively diverts blood from the weakened ventricle and propels it to the aorta for circulation through the rest of the patient's vascular system.

FIG. 6 illustrates the mechanical circulatory support system 310 during battery 322 powered operation. A driveline 326 that exits through the patient's abdomen 328 connects the implanted blood pump assembly 314 to the external system controller 320, which monitors system 310 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 310 can be powered by either one, two, or more batteries 322. It will be appreciated that although the system controller 320 and power source 322 are illustrated outside/external to the patient body, the driveline 326, the system controller 320 and/or the power source 322 can be partially or fully implantable within the patient, as separate components or integrated with the blood pump assembly 314. Examples of such modifications are further described in U.S. Pat. No. 8,562,508 and U.S. Patent Publication No. 2013/0127253, all of which are incorporated herein by reference for all purposes in their entirety.

Figure 8:
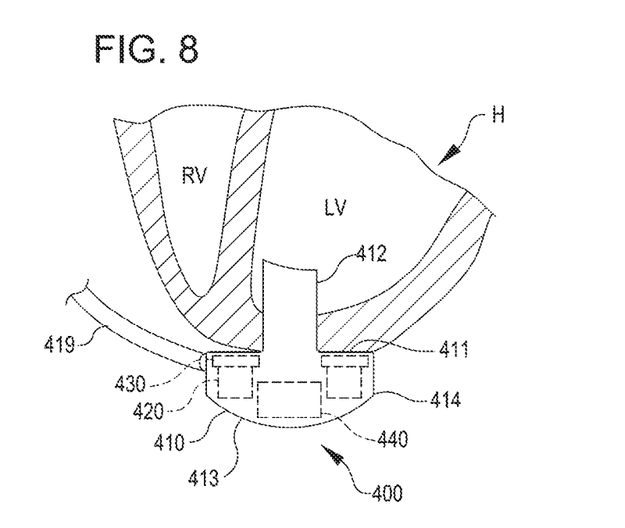
FIG. 8 is an illustration of a blood pump in an operational position implanted in a patient's body.
Figure 9:
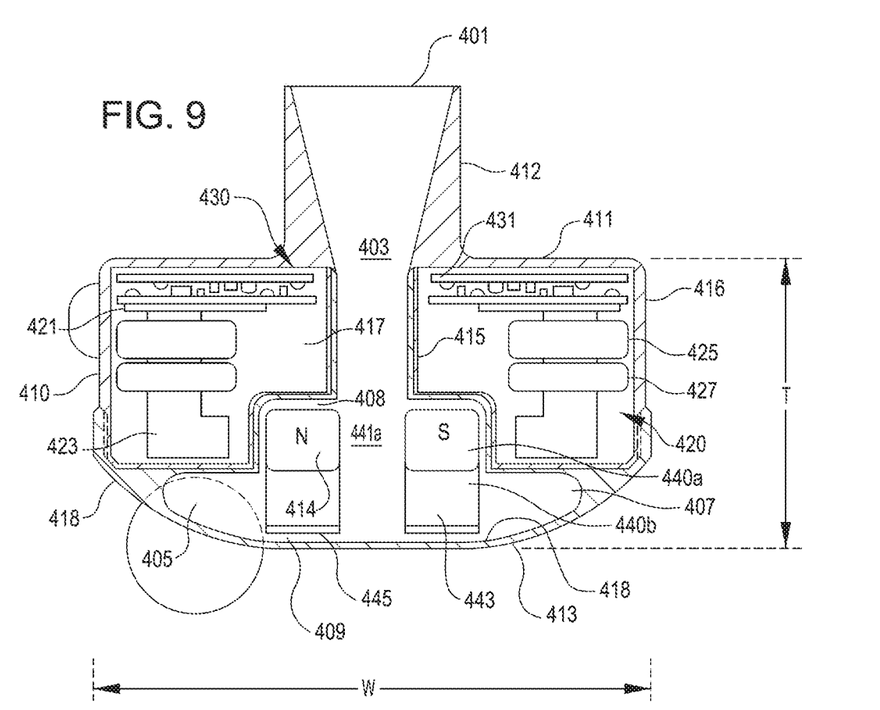
FIG. 9 is a cross-sectional view of the blood pump of FIG. 8.
Figure 10:
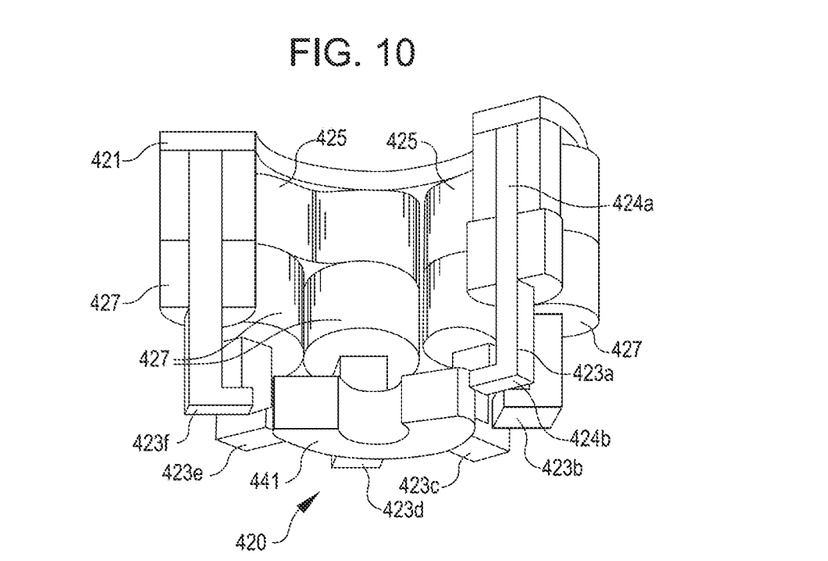
FIG. 10 is a partial cut-away perspective view of a stator of a blood pump.

With reference to FIG. 8 to FIG. 10, a left ventricular assist blood pump assembly 400 having a circular shaped housing 410 is implanted in a patient's body with a first face 411 of the housing 410 positioned against the patient's heart H and a second face 413 of the housing 410 facing away from the heart H. The first face 411 of the housing 410 includes an inlet cannula 412 extending into the left ventricle LV of the heart H. The second face 413 of the housing 410 has a chamfered edge 414 to avoid irritating other tissue that may come into contact with the blood pump assembly 400, such as the patient's diaphragm. To construct the illustrated shape of the puck-shaped housing 410 in a compact form, a stator 420 and electronics 430 of the pump assembly 400 are positioned on the inflow side of the housing toward first face 411, and an impeller 440 of the pump assembly 400 is positioned along the second face 413. This positioning of the stator 420, electronics 430, and impeller 440 permits the edge 414 to be chamfered along the contour of the impeller 440, as illustrated in at least FIGS. 7-9, for example.

Referring to FIG. 9, the blood pump assembly 400 includes a dividing wall 415 within the housing 410 defining a blood flow conduit 403. The blood flow conduit 403 extends from an inlet opening 401 of the inlet cannula 412 through the stator 420 to an outlet opening 405 defined by the housing 410. The impeller 440 is positioned within the blood flow conduit 403. The stator 420 is disposed circumferentially about a first portion 440a of the impeller 440, for example about a permanent magnet 441. The stator 420 is also positioned relative to the impeller 440 such that, in use, blood flows within the blood flow conduit 403 through the stator 420 before reaching the impeller 440. The permanent magnet 441 has a permanent magnetic north pole N and a permanent magnetic south pole S for combined active and passive magnetic levitation of the impeller 440 and for rotation of the impeller 440. The impeller 440 also has a second portion 440b that includes impeller blades 443. The impeller blades 443 are located within a volute 407 of the blood flow conduit such that the impeller blades 443 are located proximate to the second face 413 of the housing 410.

The puck-shaped housing 410 further includes a peripheral wall 416 that extends between the first face 411 and a removable cap 418. As illustrated, the peripheral wall 416 is formed as a hollow circular cylinder having a width W between opposing portions of the peripheral wall 416. The housing 410 also has a thickness T between the first face 411 and the second face 413 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 416 encloses an internal compartment 417 that surrounds the dividing wall 415 and the blood flow conduit 403, with the stator 420 and the electronics 430 disposed in the internal compartment 417 about the dividing wall 415. The removable cap 418 includes the second face 413, the chamfered edge 414, and defines the outlet opening 405. The cap 418 can be threadedly engaged with the peripheral wall 416 to seal the cap 418 in engagement with the peripheral wall 416. The cap 418 includes an inner surface 418a of the cap 418 that defines the volute 407 that is in fluid communication with the outlet opening 405.

Within the internal compartment 417, the electronics 430 are positioned adjacent to the first face 411 and the stator 420 is positioned adjacent to the electronics 430 on an opposite side of the electronics 430 from the first face 411. The electronics 430 include circuit boards 431 and various components carried on the circuit boards 431 to control the operation of the pump 400 (e.g., magnetic levitation and/or drive of the impeller) by controlling the electrical supply to the stator 420. The housing 410 is configured to receive the circuit boards 431 within the internal compartment 417 generally parallel to the first face 411 for efficient use of the space within the internal compartment 417. The circuit boards also extend radially-inward towards the dividing wall 415 and radially-outward towards the peripheral wall 416. For example, the internal compartment 417 is generally sized no larger than necessary to accommodate the circuit boards 431, and space for heat dissipation, material expansion, potting materials, and/or other elements used in installing the circuit boards 431. Thus, the external shape of the housing 410 proximate the first face 411 generally fits the shape of the circuits boards 431 closely to provide external dimensions that are not much greater than the dimensions of the circuit boards 431.

With continued reference to FIG. 9 and FIG. 10, the stator 420 includes a back iron 421 and pole pieces 423a-423f arranged at intervals around the dividing wall 415. The back iron 421 extends around the dividing wall 415 and is formed as a generally flat disc of a ferromagnetic material, such as steel, in order to conduct magnetic flux. The back iron 421 is arranged beside the control electronics 430 and provides a base for the pole pieces 423a-423f.

Each of the pole piece 423a-423f is L-shaped and has a drive coil 425 for generating an electromagnetic field to rotate the impeller 440. For example, the pole piece 423a has a first leg 424a that contacts the back iron 421 and extends from the back iron 421 towards the second face 413. The pole piece 423a can also have a second leg 424b that extends from the first leg 424a through an opening of a circuit board 431 towards the dividing wall 415 proximate the location of the permanent magnet 441 of the impeller 440. In an aspect, each of the second legs 424b of the pole pieces 423a-423f is sticking through an opening of the circuit board 431. In an aspect, each of the first legs 424a of the pole pieces 423a-423f is sticking through an opening of the circuit board 431. In an aspect, the openings of the circuit board are enclosing the first legs 424a of the pole pieces 423a-423f.

In a general aspect, the implantable blood pump 400 can include one or more Hall sensors that may provide an output voltage, which is directly proportional to a strength of a magnetic field that is located in between at least one of the pole pieces 423a-423f and the permanent magnet 441, and the output voltage may provide feedback to the control electronics 430 of the pump 400 to determine if the impeller 440 and/or the permanent magnet 441 is not at its intended position for the operation of the pump 400. For example, a position of the impeller 440 and/or the permanent magnet 441 can be adjusted, e.g., the impeller 440 or the permanent magnet 441 may be pushed or pulled towards a center of the blood flow conduit 403 or towards a center of the stator 420.

Each of the pole pieces 423a-423f also has a levitation coil 427 for generating an electromagnetic field to control the radial position of the impeller 440. Each of the drive coils 425 and the levitation coils 427 includes multiple windings of a conductor around the pole pieces 423a-423f. Particularly, each of the drive coils 425 is wound around two adjacent ones of the pole pieces 423, such as pole pieces 423d and 423e, and each levitation coil 427 is wound around a single pole piece. The drive coils 425 and the levitation coils 427 are wound around the first legs of the pole pieces 423, and magnetic flux generated by passing electrical current though the coils 425 and 427 during use is conducted through the first legs and the second legs of the pole pieces 423 and the back iron 421. The drive coils 425 and the levitation coils 427 of the stator 420 are arranged in opposing pairs and are controlled to drive the impeller and to radially levitate the impeller 440 by generating electromagnetic fields that interact with the permanent magnetic poles S and N of the permanent magnet 441. Because the stator 420 includes both the drive coils 425 and the levitation coils 427, only a single stator is needed to levitate the impeller 440 using only passive and active magnetic forces. The permanent magnet 441 in this configuration has only one magnetic moment and is formed from a monolithic permanent magnetic body 441. For example, the stator 420 can be controlled as discussed in U.S. Pat. No. 6,351,048, the entire contents of which are incorporated herein by reference for all purposes. The control electronics 430 and the stator 420 receive electrical power from a remote power supply via a cable 419 (FIG. 8). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The impeller 440 is arranged within the housing 410 such that its permanent magnet 441 is located upstream of impeller blades in a location closer to the inlet opening 401. The permanent magnet 441 is received within the blood flow conduit 403 proximate the second legs 424b of the pole pieces 423 to provide the passive axial centering force though interaction of the permanent magnet 441 and ferromagnetic material of the pole pieces 423. The permanent magnet 441 of the impeller 440 and the dividing wall 415 form a gap 408 between the permanent magnet 441 and the dividing wall 415 when the impeller 440 is centered within the dividing wall 415. The gap 408 may be from about 0.2 millimeters to about 2 millimeters. For example, the gap 408 can be approximately 1 millimeter. The north permanent magnetic pole N and the south permanent magnetic pole S of the permanent magnet 441 provide a permanent magnetic attractive force between the impeller 440 and the stator 420 that acts as a passive axial centering force that tends to maintain the impeller 440 generally centered within the stator 420 and tends to resist the impeller 440 from moving towards the first face 411 or towards the second face 413. When the gap 408 is smaller, the magnetic attractive force between the permanent magnet 441 and the stator 420 is greater, and the gap 408 is sized to allow the permanent magnet 441 to provide the passive magnetic axial centering force having a magnitude that is adequate to limit the impeller 440 from contacting the dividing wall 415 or the inner surface 418a of the cap 418. The impeller 440 also includes a shroud 445 that covers the ends of the impeller blades 443 facing the second face 413 that assists in directing blood flow into the volute 407. The shroud 445 and the inner surface 418a of the cap 418 form a gap 409 between the shroud 445 and the inner surface 418a when the impeller 440 is levitated by the stator 420. The gap 409 is from about 0.2 millimeters to about 2 millimeters. For example, the gap 409 is approximately 1 millimeter.

As blood flows through the blood flow conduit 403, blood flows through a central aperture 441a formed through the permanent magnet 441. Blood also flows through the gap 408 between the impeller 440 and the dividing wall 415 and through the gap 409 between the shroud 445 and the inner surface 408a of the cap 418. The gaps 408 and 409 are large enough to allow adequate blood flow to limit clot formation that may occur if the blood is allowed to become stagnant. The gaps 408 and 409 are also large enough to limit pressure forces on the blood cells such that the blood is not damaged when flowing through the pump 400. As a result of the size of the gaps 108 and 109 limiting pressure forces on the blood cells, the gaps 408 and 409 are too large to provide a meaningful hydrodynamic suspension effect. That is to say, the blood does not act as a bearing within the gaps 408 and 409, and the impeller is only magnetically-levitated. In various embodiments, the gaps 408 and 409 are sized and dimensioned so the blood flowing through the gaps forms a film that provides a hydrodynamic suspension effect. In this manner, the impeller can be suspended by magnetic forces, hydrodynamic forces, or both.

Because the impeller 440 is radially suspended by active control of the levitation coils 427 as discussed above, and because the impeller 440 is axially suspended by passive interaction of the permanent magnet 441 and the stator 420, no impeller levitation components are needed proximate the second face 413. The incorporation of all the components for impeller levitation in the stator 420 (i.e., the levitation coils 427 and the pole pieces 423) allows the cap 418 to be contoured to the shape of the impeller blades 443 and the volute 407. Additionally, incorporation of all the impeller levitation components in the stator 420 eliminates the need for electrical connectors extending from the compartment 417 to the cap 418, which allows the cap to be easily installed and/or removed and eliminates potential sources of pump failure.

In use, the drive coils 425 of the stator 420 generates electromagnetic fields through the pole pieces 423 that selectively attract and repel the magnetic north pole N and the magnetic south pole S of the impeller 440 to cause the impeller 440 to rotate within stator 420. For example, the one or more Hall sensors may sense a current position of the impeller 440 and/or the permanent magnet 441, wherein the output voltage of the one or more Hall sensors may be used to selectively attract and repel the magnetic north pole N and the magnetic south pole S of the impeller 440 to cause the impeller 440 to rotate within stator 420. As the impeller 440 rotates, the impeller blades 443 force blood into the volute 407 such that blood is forced out of the outlet opening 405. Additionally, the impeller draws blood into pump 400 through the inlet opening 401. As blood is drawn into the blood pump by rotation of the impeller blades 443 of the impeller 440, the blood flows through the inlet opening 401 and flows through the control electronics 430 and the stator 420 toward the impeller 440. Blood flows through the aperture 441a of the permanent magnet 441 and between the impeller blades 443, the shroud 445, and the permanent magnet 441, and into the volute 407. Blood also flows around the impeller 440, through the gap 408 and through the gap 409 between the shroud 445 and the inner surface 418a of the cap 418. The blood exits the volute 407 through the outlet opening 405, which may be coupled to an outflow cannula.

Figure 11:
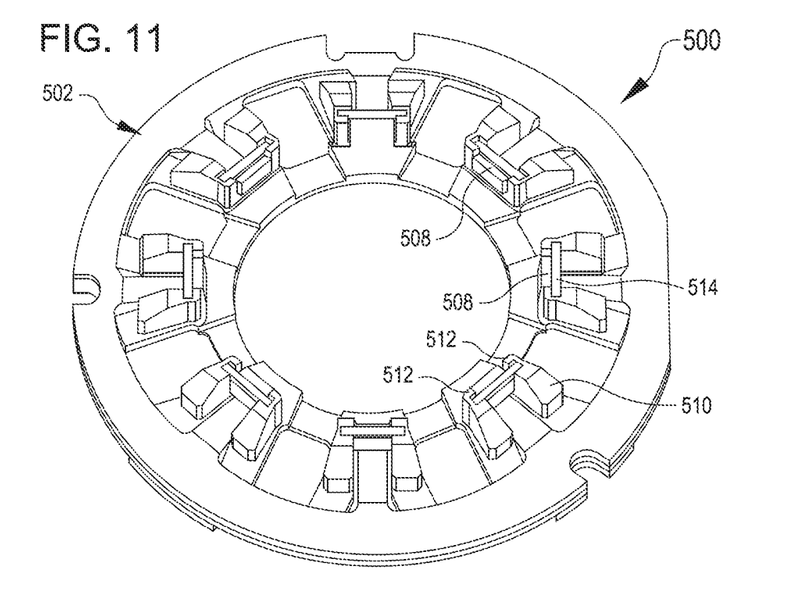
FIG. 11 is an illustration of an embodiment of a Hall Sensor assembly for the blood pump of FIG. 8.

FIG. 11 shows a Hall Sensor assembly 500 for the blood pump assembly 314, in accordance with many embodiments. The Hall Sensor assembly 500 includes a printed circuit board (PCB) 502 and individual Hall Effect sensors 508 supported by the printed circuit board 502. Eight axi-symmetric Hall Effect sensors 508 are placed in a rigid, plastic mechanical carrier 510 and the PCB 502 is placed onto the mechanical carrier 510. The mechanical carrier 510 uses guide rails 512 to locate electrically neutral rigid PCB portions 514 attached to the top edges of the Hall Effect sensors 508 and to locate the PCB 502.

The Hall Effect sensors 508 are configured to transduce a position of the impeller 440 of the pump 400. In the illustrated embodiment, the Hall Effect sensors 508 are supported so as to be standing orthogonally relative to the PCB 502 and a longest edge of each of the Hall Effect sensors 508 is aligned to possess an orthogonal component with respect to the surface of the PCB 502. Each of the Hall Effect sensors 508 generate an output voltage, which is directly proportional to a strength of a magnetic field that is located in between at least one of the pole pieces 423a-423f and the permanent magnet 441. The voltage output by each of the Hall Effect sensors 508 is received by the control electronics 430, which processes the sensor output voltages to determine the position and orientation of the impeller 440. The determined position and orientation of the impeller 440 is used to determine if the impeller 440 is not at its intended position for the operation of the pump 400. For example, a position of the impeller 440 and/or the permanent magnet 441 may be adjusted, for example, the impeller 440 or the permanent magnet 441 may be pushed or pulled towards a center of the blood flow conduit 403 or towards a center of the stator 420. The determined position of the impeller 440 can also be used to determine impeller eccentricity or a target impeller eccentricity and/or a position along the blood flow conduit 403. The position along the blood flow conduit 403 can be used as described herein in combination with rotation rate of the impeller 440 to estimate flow rate of blood pumped by the blood pump assembly 400, as would be understood by one of skill from the description herein.

Figure 12:
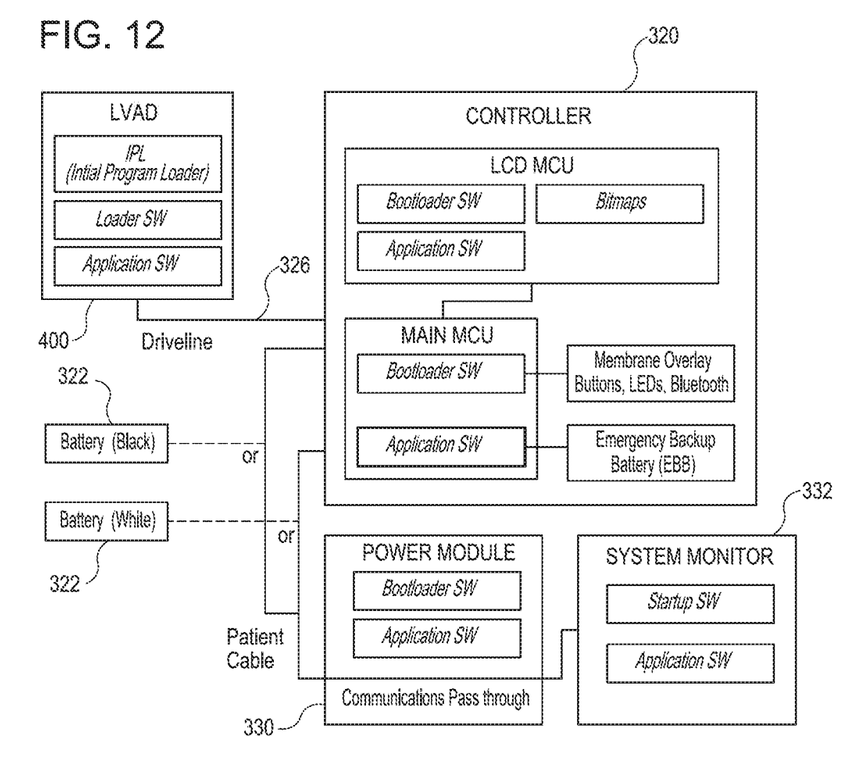
FIG. 12 is a schematic diagram of a control system architecture of the mechanical support system of FIG. 6.

FIG. 12 is a schematic diagram of a control system architecture of the mechanical support system of FIG. 6. The driveline 426 couples the implanted blood pump assembly 400 to the external system controller 420, which monitors system operation via various software applications. The blood pump assembly 400 itself also includes several software applications that are executable by the on board electronics 430 (e.g., processors, ASICs, etc.) for various functions, such as to control radial levitation and/or drive of the impeller of the pump assembly 400 during operation. The external system controller 320 can in turn be coupled to batteries 322 or a power module 330 that connect to an AC electrical outlet. The external system controller 320 can also include an emergency backup battery (EBB) to power the system (e.g., when the batteries 322 are depleted) and a membrane overlay, including Bluetooth capabilities for wireless data communication. An external computer having a system monitor 332 that is configurable by an operator, such as clinician or patient, may further be coupled to the circulatory support system for configuring the external system controller 320, implanted blood pump assembly 400, and/or patient specific parameters, updating software on the external system controller 320 and/or implanted blood pump assembly 400, monitoring system operation, and/or as a conduit for system inputs or outputs.

Figure 13:
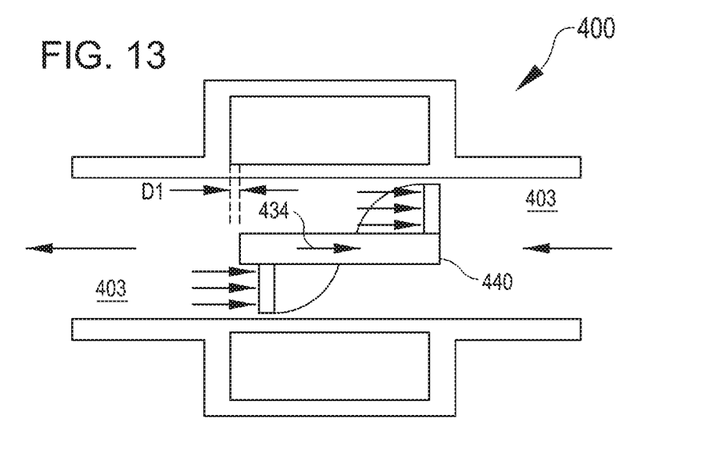
FIG. 13 and FIG. 14 are simplified schematic diagrams illustrating a blood pump in which a motor stator used to rotate and magnetically position the impeller within a blood flow channel of the blood pump and a deflection of the impeller along the blood flow channel is used to determine thrust applied to the impeller, in accordance with many embodiments.
Figure 14:
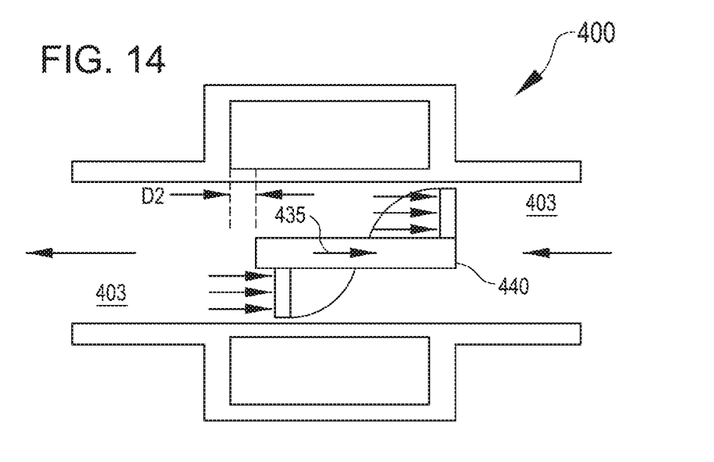

FIG. 13 is a simplified schematic diagram illustrating a first axial displacement (D1) of the impeller 440 (relative to a reference axial position of the impeller 440 with zero thrust load applied) that is induced by a first thrust load 434 applied to the impeller 440. FIG. 14 is a simplified schematic diagram illustrating a second axial displacement (D2) of the impeller 440, which is greater than the first axial displacement (D1), that is induced by a second thrust load 435, which is greater than the first thrust loads 434. As described herein, the axial displacement of the impeller 440 (relative to the reference axial position of the impeller with zero thrust load applied) varies as a function of the magnitude of the thrust load applied to the impeller 440. In many embodiments, the blood pump assembly 400 includes one or more sensors configured to generate output indicative of the axial position of the impeller 440, and thereby indicative of the thrust load applied to the impeller 440. For example, the output of the Hall Sensor assembly 500 can be processed to determine the axial displacement of the impeller 440 and thereby determine the thrust load applied to the impeller. The blood pump assembly 400 can also include one or more sensors configured to monitor the axial position of the impeller 440 and thereby monitor the thrust load applied to the impeller. For example, the blood pump assembly 400 can include one or more Hall-Effect sensors supported by the housing (e.g., adjacent a circumferential wall of the blood flow conduit 403 or in an inlet stator disposed in the blood flow conduit 403) that generates an output signal indicative of the axial position of the impeller 440 along the blood flow conduit 403. The axial position of the impeller 440 can then be processed by the controller to determine a thrust load applied to the impeller 440. As already described herein, the thrust load applied to the impeller 440 and the rotational rate of the impeller 440 can then be used by the controller to determine a flow rate of blood pumped by the blood pump 400.

Pump Induced Pressure in Patient

Figure 15:
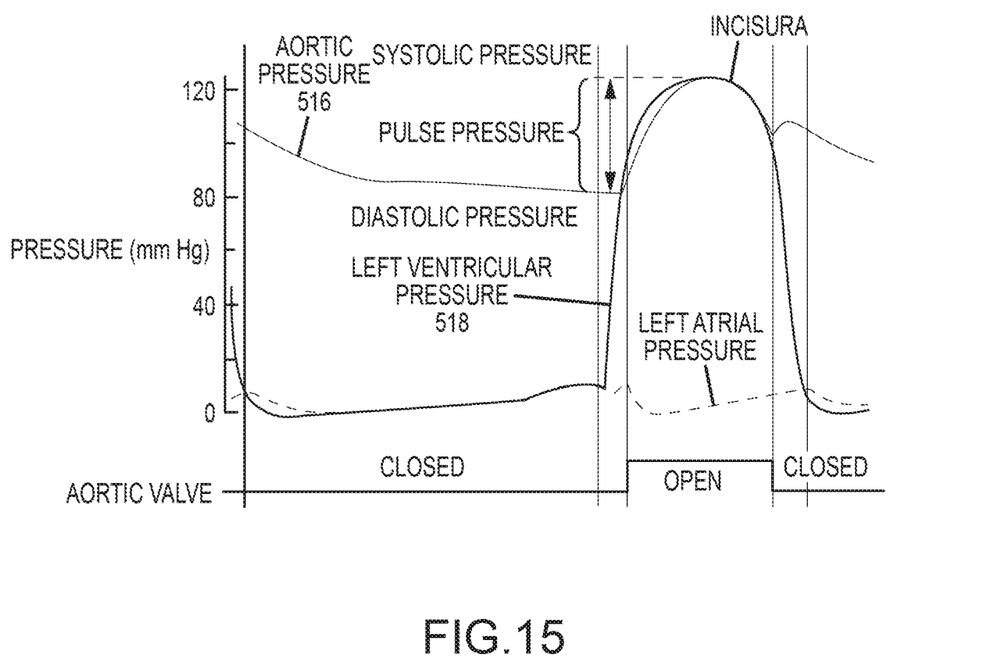
FIG. 15 shows example aortic pressure and left ventricular pressure over a heart cycle.

As discussed herein, the thrust load from the impeller is indicative of the pressure differential across the pump. In many embodiments, the pressure differential across the pump is output to a suitable output device (e.g., a display, speaker) to inform the patient and/or a medical professional involved in the treatment of the patient with regard to a resulting pressure differential within the patient. For example, in the embodiment illustrated in FIG. 6, the blood pump 314 is attached to an apex of the left ventricle and pumps blood from the left ventricle to the patient's aorta. The pressure differential across the blood pump 314 is the difference between the left ventricular pressure and the aortic pressure. The pressure across the pump is therefore the same as the pressure across the aortic valve. FIG. 15 shows example aortic pressure 516 and left ventricular pressure 518 over a heart cycle. During contraction of the left ventricle, the left ventricular pressure 518 increases from below the aortic pressure 516. When the left ventricular pressure 518 equals and exceeds the aortic pressure 516, the aortic valve opens to enable ejection of blood from the left ventricle into the aorta. At the end of the ejection of blood from the left ventricle, the left ventricular pressure 518 drops below the aortic pressure 516 thereby closing the aortic valve. By outputting the pressure differential across the pump to a suitable output device, the user and/or the medical professional is provided with information (e.g., pressure across the aortic valve when the blood pump is used as an LVAD) helpful in understanding the functioning of the patient's heart.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A circulation assist system comprising:
   a centrifugal blood pump comprising:
   a housing forming a blood flow channel;
   an impeller disposed within the blood flow channel;
   a motor stator mounted to the housing and operable to magnetically rotate the impeller, wherein the motor stator comprises levitation coils via which a radial position of the impeller within the blood flow channel is controlled, and wherein a thrust load applied to the impeller by blood impelled through the blood flow channel by the impeller is reacted by the motor stator; and
   Hall-Effect sensors configured to generate output indicative of an eccentricity and a position of the impeller within the blood flow channel, wherein the Hall-Effect sensors surround a circumferential wall of the blood flow channel; and
   a controller operatively coupled with the motor stator and the Hall-Effect sensors, wherein the controller is configured to determine a rotational rate of the impeller and process the rotational rate of the impeller and the output generated by the Hall-Effect sensors to estimate at least one of:
   the thrust load applied to the impeller;
   a pressure differential of the blood impelled through the blood flow channel; or
   a flow rate of the blood impelled through the blood flow channel.

2. The circulation assist system of claim 1, wherein the controller is configured to process the output generated by the Hall-Effect sensors to determine the rotational rate of the impeller.

3. The circulation assist system of claim 2, wherein the controller is configured to estimate the flow rate of the blood impelled through the blood flow channel.

4. The circulation assist system of claim 1, wherein the controller is configured to estimate the pressure differential of the blood impelled through the blood flow channel.

5. The circulation assist system of claim 4, wherein:
   the centrifugal blood pump is configured to pump blood from a patient's left ventricle to the patient's aorta; and
   the pressure differential of the blood impelled through the blood flow channel corresponds to a pressure difference between the patient's left ventricle and the patient's aorta.

6. The circulation assist system of claim 4, wherein the controller is configured to estimate the thrust load applied to the impeller.

7. The circulation assist system of claim 4, wherein the controller is configured to process the output generated by the Hall-Effect sensors to determine the rotational rate of the impeller.

8. The circulation assist system of claim 7, wherein the controller is configured to estimate the thrust load applied to the impeller.

9. The circulation assist system of claim 1, wherein the controller is configured to estimate the thrust load applied to the impeller.

10. A method for estimating one or more blood flow related parameters in a blood circulation assist system, the method comprising:
    controlling a motor stator to magnetically rotate an impeller within a blood flow channel of a centrifugal blood pump and magnetically levitate the impeller within the blood flow channel so as to control a radial position of the impeller within the blood flow channel;
    magnetically reacting a thrust load applied to the impeller by blood impelled through the blood flow channel by the impeller via the motor stator;
    generating output by Hall-Effect sensors indicative of an eccentricity and a position of the impeller within the blood flow channel;
    determining, by a controller, a rotational rate of the impeller;
    processing the rotational rate of the impeller and the output of the Hall-Effect sensors, by the controller, to estimate at least one of:
    the thrust load applied to the impeller;
    a pressure differential of the blood impelled through the blood flow channel; or
    a flow rate of the blood impelled through the blood flow channel.

11. The method of claim 10, wherein the controller determines the rotational rate of the impeller based on the output generated by the Hall-Effect sensors.

12. The method of claim 11, wherein the controller estimates the flow rate of the blood impelled through the blood flow channel.

13. The method of claim 10, wherein the controller estimates the pressure differential of the blood impelled through the blood flow channel.

14. The method of claim 13, wherein:
    the centrifugal blood pump is configured to pump blood from a patient's left ventricle to the patient's aorta; and
    the pressure differential of the blood impelled through the blood flow channel corresponds to a pressure difference between the patient's left ventricle and the patient's aorta.

15. The method of claim 10, wherein the controller estimates the thrust load applied to the impeller.

16. The method of claim 15, wherein the controller estimates the rotational rate of the impeller based on the output generated by the Hall-Effect sensors.

17. The method of claim 16, wherein the controller estimates flow rate of the blood impelled through the blood flow channel.

18. The method of claim 17, wherein the controller estimates the pressure differential of the blood impelled through the blood flow channel.

19. The method of claim 18, wherein:
    the centrifugal blood pump is configured to pump blood from a patient's left ventricle to the patient's aorta; and
    the pressure differential of the blood impelled through the blood flow channel corresponds to a pressure difference between the patient's left ventricle and the patient's aorta.

* * * * *